(12) United States Patent
Gordon et al.

(10) Patent No.: US 6,458,580 B1
(45) Date of Patent: Oct. 1, 2002

(54) FUNGAL SULPHUR SOURCE AND METHOD OF USING THE SAME

(75) Inventors: Geoffrey Leslie Raymond Gordon, New South Wales (AU); Michael William Phillips, New South Wales (AU)

(73) Assignees: Commonwealth Scientific and Industrial Research Organisation, Campbell (AU); Australian Wool Research and Promotion Organization, Parkville (AU)

( * ) Notice: Subject to any disclaimer, the term of this patent is extended or adjusted under 35 U.S.C. 154(b) by 0 days.

(21) Appl. No.: 09/601,337

(22) PCT Filed: Feb. 10, 1998

(86) PCT No.: PCT/AU98/00075

§ 371 (c)(1), (2), (4) Date: Sep. 27, 2000

(87) PCT Pub. No.: WO98/42326

PCT Pub. Date: Oct. 1, 1998

(30) Foreign Application Priority Data

Mar. 21, 1997 (AU) .............................................. PO5793

(51) Int. Cl.[7] .............................. C12N 1/14; C12N 1/00; C12N 1/38; A23K 1/175; C07D 257/00
(52) U.S. Cl. .................... 435/254.1; 435/243; 435/294; 435/256.8; 426/74; 426/624; 426/630; 426/2; 548/251; 548/252
(58) Field of Search .............................. 426/74, 2, 251, 426/252; 424/184.1; 548/252; 435/254.1, 243, 244, 256.8

(56) References Cited

U.S. PATENT DOCUMENTS 3,711,289  1/1973  Miller .............................. 99/2
4,423,224  12/1983  Marecki et al. .............. 548/252
4,564,524  1/1986  Haarasilta ..................... 426/74
4,957,748  9/1990  Winowiski ..................... 426/2
5,023,091  6/1991  Winowiski ..................... 426/2

FOREIGN PATENT DOCUMENTS

FR            2290158       6/1976    ............ A23K/1/22

OTHER PUBLICATIONS

Phillips, M. W. and Gordon, G.L.R., Growth Response Reduce Sulphur Compounds of a Ruminal Fungus, Neocallimastix SP. LM1 Abstract. 1991.

Akin et al, Applied and Environmental Microbiology, vol. 46, No. 3, "Rumen Bacterial and Fungal . . . ", pp. 738–748, Sep. 1983.

Buttrey et al, J. Anim. Science, vol. 63, "Effect of Sulfur Fertilization on Chemical . . . ", pp. 1236–1245, 1986.

Marvin–Sikkema et al, Journal of Gen Microbiology, vol. 138, "Characterization of an anaerobic . . . ", pp. 2235–2241, 1992.

Onoda et al, Reprod Nutr Dev., vol. 36, No. 3,"Effects of amino acids on the growth of an . . . ", pp. 311–320, 1996.

Qi et al, J. Anim Science, vol. 70, No. 9, "Sulfate Supplementatin of Angora Goats: Metabolic . . . ", pp. 2828–2837, 1992.

Qi et al , J. Anim Science, vol. 70, No. 11, "Sulfate Supplementation of Alpine Goats: Effects . . . ", pp. 3541–3550, 1992.

Merchen et al, J. Anim Science, vol. 70, No. 10, "Manipulation of Amino Acid Supply to the Growing . . . ", pp. 3238–3247,1992.

*Primary Examiner*—Lynette R. F. Smith
*Assistant Examiner*—Khatol S Shahnan-Shah
(74) *Attorney, Agent, or Firm*—Jacobson Holman, PLLC

(57) ABSTRACT

A method for promoting the growth of at least one anaerobic fungus in the rumen of a ruminant animal, the method comprising the step of administering to the rumen an effective amount of a degradation resistant sulphur source.

17 Claims, 2 Drawing Sheets

FUNGAL SULPHUR SOURCE AND METHOD OF USING THE SAME

BACKGROUND

The present invention relates to a sulphur source for fungi and a method for using the same to promote the growth of fungi in the rumen of a ruminant animal. More particularly, the present invention relates to a method for promoting the growth of anaerobic fungi in the rumen of animals fed on low sulphur content diets.

The rumen or forestomach is an organ found in the digestive tract of certain herbivorous mammals. The rumen is located prior to the gastric stomach and is the site where digestion and fermentation of plant material occurs through the activity of microbial populations.

Anaerobic fungi, bacteria and protozoa represent the three major groups of microorganisms in the rumen. The anaerobic fungi make a vital contribution to the digestion of plant fibre and in particular, plant fibre in poor or low quality feed. Poor quality feed often lacks one or more dietary components which may affect the microbial populations in the rumen. In particular, when ruminant animals consume a low sulphur content diet the population of anaerobic fungi in the rumen may be significantly reduced. A reduction in the fungi population can hamper the digestion of feed which in turn may reduce feed intake and cause the animal to have a reduced productivity.

Fungi in the rumen require sulphur in reduced form to meet their growth requirements. When sulphur is administered to the rumen as dietary sulphur it is mostly degraded to sulphide by bacteria and used by fungi and other microorganisms in the rumen. Any remaining sulphide is transported across the rumen wall and out of the rumen. Thus, sulphide does not persist in the rumen.

The effect of low sulphur diets on the population of anaerobic fungi in the rumen was observed in 1983. Since that time a number of sulphur sources have been used to supplement the diet of ruminant animals fed on low sulphur diets. For example, sulphur in the form of sodium sulphate has been added directly to feed sources such as pastures with low sulphur contents, and the sulphur containing amino acid, methionine, has been administered to animals as a feed supplement.

Whilst the prior art sulphur sources outlined above have been found to promote the growth of ruminant fungi and increase the intake of feed by ruminant animals, they are degraded to sulphide by bacteria in the rumen at a rate that is greater than the rate at which the fungi in the rumen use the resulting sulphide. Thus, a large amount of the sulphide produced is not used by the fungi.

The rate of degradation of the prior art sulphur sources, and to a certain extent their mode of administration, means that relatively large amounts need to be administered to deliver an effective dose of sulphur to fungi in the rumen of a ruminant animal. The large amounts of the sulphur sources used cause the methods to be relatively expensive and inefficient.

The present invention seeks to overcome or at least partially alleviate the problems identified above.

SUMMARY OF THE INVENTION

The present invention provides a method for promoting the growth of at least one anaerobic fungus in the rumen of a ruminant animal, the method comprising the step of administering to the rumen an effective amount of a degradation resistant sulphur source.

Throughout this specification, unless the context requires otherwise, the word "comprise", or variations such as "comprises" or "comprising" will be understood to imply the inclusion of a stated integer or group of integers, but not the exclusion of any other integer or group of integers including method steps.

Further, throughout the following description reference will be made to "ruminant animals" which will be understood to include all ruminant and ruminant-like animals, being members of the Order Artiodactyl and having a pre-gastric fermentation in a rumen (for ruminant animals), or a similar part of the digestive tract such as the paunch (for ruminant-like animals).

For the purposes of the present invention the term "degradation resistant" is to be interpreted in terms of the microbial population in the rumen. Thus, a "degradation resistant sulphur source" is a sulphur source that is degraded by microorganisms in the rumen, such as bacteria, to sulphide at a slower rate than the prior art sulphur sources so that it remains available to fungi for a longer period of time.

The degradation resistant sulphur source may be varied. Preferably, the degradation resistant sulphur source is 3-mercaptopropanoic acid (MPA) or a functional equivalent thereof. Functional equivalents for the purposes of the present invention include; the salts of MPA with monovalent and divalent cations such as sodium, potassium, calcium, copper, zinc and magnesium salts; the esters of MPA incorporating alkyl groups such as methyl, ethyl and butyl groups and; the dimer form of MPA, in which two MPA monomers are linked by a disulphide bond.

The sulphur source may be administered in any of a number of ways apparent to one skilled in the art. Preferably, the sulphur source is administered intra-ruminally or orally as a feed supplement. When the sulphur source is administered intra-ruminally, it is preferably administered using a controlled release device such as the device described in Australian patent 555998.

The degradation resistant nature of the sulphur source of the present invention allows it to be administered in smaller doses and less often relative to other sulphur sources. In this respect, the sulphur source of the present invention is degraded by microorganisms such as bacteria in the rumen at a slower rate than the prior art sulphur sources and thus continues to be available in the rumen for longer periods of time.

The effective dose may be varied and may be at least partially dependent on the type of ruminant animal receiving the dose and the amount of sulphur the animal is extracting from its regular intake of feed. In this respect, it is expected that the larger the animal receiving the dose, the larger the dose of the sulphur source required to constitute an effective amount will be. Similarly, the higher the sulphur content of a given feed, the smaller the dose of the sulphur source required to constitute an effective amount will be. It will be appreciated that the optimum dose for a particular animal could be readily determined by one skilled in the relevant art.

Preferably, the effective dose of MPA is such that the concentration of MPA in the rumen is approximately 0.2 mM to 8 mM. Even more preferably, the effective dose of MPA is such that the concentration of MPA in the rumen is approximately 0.2 to 4 mM. In one particularly preferred form, the effective dose of MPA is such that the concentration of MPA in the rumen is approximately 0.75 to 1.5 mM.

The effective dose required to produce the MPA concentrations outlined above varies. Preferably, and when the ruminant animal is a sheep, the effective dose is approximately 25–200 mg Sulphur/day or more preferably, approximately 95–190 mg Sulphur/day. For example, when the sulphur source is MPA and the ruminant animal is a sheep fed on a low sulphur diet (approximately 0.06% sulphur), the effective dose of MPA is preferably approximately 190 mg Sulphur/day.

The method of the invention makes it possible for animals to have an improved productivity. In this respect, and as will be illustrated in the examples below, animals to which the method is applied show improved voluntary feed intake, dry matter digestibility and dry matter digested. The improvement in these characteristics correlates to improved productivity compared to those same animals when not subjected to the method of the invention.

The present invention also provides a veterinary preparation comprising a degradation resistant sulphur source and a suitable carrier.

Figure 1:
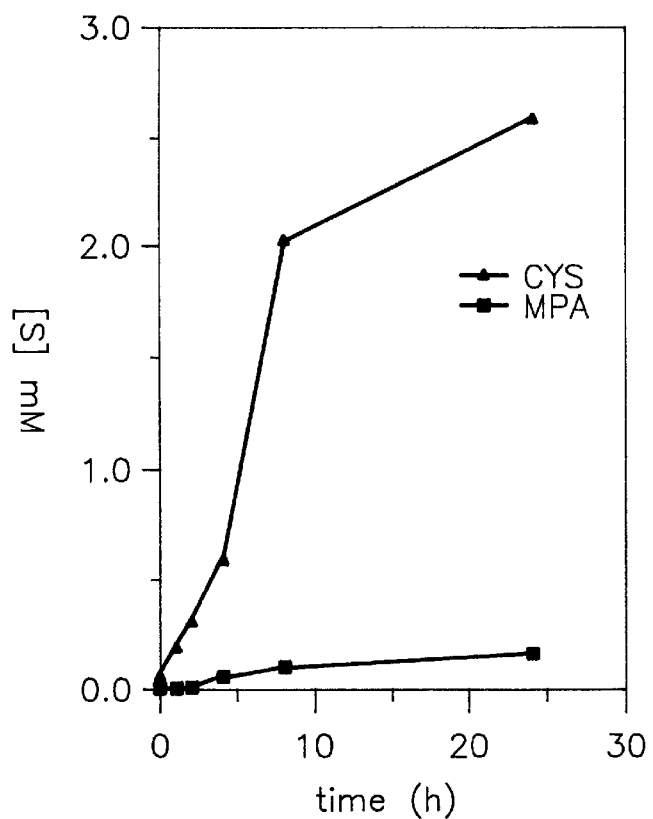
FIG. 1 is a graph illustrating in vitro degradation of MPA and cysteine by rumen microbes.

The present invention will now be described with reference to the following examples. The description of the examples is in no way to limit the scope of the preceding description.

EXAMPLES

Example 1

In vitro Growth of a Representative Anaerobic Fungus (Neocallimastix sp.LM1) using Different Compounds as the Sole Source of Sulphur.

Fungi were tested by subculture in media that had only trace levels of sulphur.

The medium was a modification of standard media for the growth of anaerobic fungi with the following changes:

the media contained no rumen fluid nor peptone (an amino acid mix without sulphur amino acids was added);

yeast extract is added at 17 mg/100 ml (rather than 52 mg/100 ml for standard media);

a trace minerals mix and vitamins mix were added;

no sulphur reductant was included but a sterile solution of titanium nitrilotriacetate was added to sterilised media (at final concentration of 1 mM) as the reductant;

subculture media had cellobiose added at 0.2% concentration and 0.5% added for the test media; and media were prepared with a $CO_2$/carbonate buffering system and dispensed in Hungate test tubes and autoclaved.

The test compounds were added at a concentration of 0.5 mM and the test tubes injected with a 5% inoculum of fungi. The fungi were subcultured twice in the media with the final culture containing 0.5% carbohydrate. After five days of incubation at 39° C. the pH of the media were determined. As the fungi are fermentative, with the major end-products organic acids, the pH of the media decreases with increasing growth: the more the growth the greater the change of pH ($\Delta pH$). To make comparisons easier the $\Delta pH$ has been multiplied by a 100. Any $\Delta pH$ (×100) below 15 represents negligible growth.

The majority of test compounds were also screened in a previous experiment. Where compounds were tested previously the results have been adjusted relative to a positive control (sodium sulphide).

The ability of a range of sulphur containing compounds to act as the sole sulphur source is given in Table 1. MPA gave growth comparable to sodium sulphide and somewhat better than cysteine. Dimethyl disulphide gave better growth and this may be due to this compound containing two sulphur atoms.

TABLE 1

| Test Compound | Relative Growth ($\Delta pH \times 100$) |
| --- | --- |
| Dimethyl disulfide | 96 |
| 3-Mercaptopropanoic acid | 79 |
| Sodium Sulphide | 75 |
| Cysteine (HCl) | 56 |
| Methyl 3-mercaptopropanoic acid | 47 |
| Mercaptopropanesulfonic acid | 45 |
| Homocysteine thiolactone | 41 |
| Homocysteine | 40 |
| Methionine | 39 |
| 2-Mercaptopropanoic acid | 31 |
| Methionine sulfoxide | 25 |
| Thioglycollate (Sodium) | 18 |
| Methyl cysteine | 16 |
| Dimethyl sulfoxide | 15 |
| Ethanethiol | 14 |
| Mercaptoethane sulfinic acid | 11 |
| Cystathionine | 9 |
| Hypotaurine | 8 |
| Glutathione | 6 |
| Thioacetamide | 6 |
| Sodium sulfate | 5 |
| Sodium thiosulfate | 5 |
| Cysteic acid | 4 |
| Methionine sulfone | 4 |
| Sodium sulfite | 4 |
| Dimethyl sulfide | 4 |
| Taurine | 3 |
| Methyl thioglycollate | 3 |
| Thiourea | 2 |
| Potassium Thiocyanate | 2 |
| Ethyl thioglycollate | 2 |
| Cysteine sulfinic acid | 1 |
| Dimethyl sulfone | 1 |
| Bis-[methylthio]methane | 0 |
| Cysteamine | 0 |
| Dimercaprol | 0 |
| Ethionine | 0 |
| Propanedithiol | 0 |
| Thioacetic acid | 0 |
| Dithiothreitol | 0 |
| Mercaptoethylanime | 0 |

Example 2

Digestion of MPA in the Rumen.

The degradation of MPA and the sulphur amino acid cysteine in rumen fluid was determined by in-vitro incubations. The compound was added to low sulphur media (described in Example 1) but with the carbohydrate source being filter paper strips (1% wt/vol). A heavy inoculum of rumen digesta (33.3%) was added and the tubes incubated. At different time periods samples were taken and frozen until analyses. Degradation was determined by measuring the accumulation of sulphide in the medium. Sulphide was determined by the methylene blue reaction where the reaction product was separated and measured by HPLC.

The results of incubating 10 mM solutions of cysteine or MPA are shown in FIG. 1. The rate and extent of degradation of MPA is significantly less than that of cysteine. Similar results were obtained when digesta was taken from sheep that had been infused with MPA for 10 days.

Example 3

In vitro Growth of Selected Fungi to Different Doses of MPA

This example determines if non-indigenous fungi that are being used for inoculation experiments have a different response in growth to the sulphur supplement MPA.

Five isolates were recovered in standard media from cryopreservation and one isolate was obtained from the culture collection. Table 2 below indicates nature of isolates.

TABLE 2

| Isolate | Genus | Animal | Location |
| --- | --- | --- | --- |
| LM1 | Neocallimastix | Sheep | Prospect NSW |
| SM1 | Piromyces | Sheep | Prospect NSW |
| CS15 | Piromyces | Cattle | Prospect NSW |
| TZB2 | Piromyces | Zebra | Tipperary Nth Territory |
| TGB1 | Neocallimastix | Gemsbok | Tipperary Nth Territory |

Each isolate was transferred from standard media to a modification of the low sulphur media described in Example 1. Carbohydrates (glucose+cellobiose) were added to give either 0.2% (in subculture phase ) or 0.5% (in test phase)

For each isolate replicate tubes of low sulphur media containing the following MPA concentrations (0, 0.2, 0.8 mM) were prepared by inoculating with dilutions of a 40 mM stock MPA solution [made up in boiled/Nitrogen bubble water and filter (0.2 $\mu$) sterilised]. Triplicate tubes of the three concentrations were inoculated with each isolate and after 3–4 days subcultured using the tubes with the best apparent growth. This set-up was repeated again and then isolates were inoculated into media containing 0.5% carbohydrate and the following MPA concentrations (mM; the subculture used in square brackets), 0 [0], 0.1, 0.2 [0.2], 0.4, 0.8, 1.2, 1.6 [0.8]. This was to be the final assessment however as some growth was obtained in the 0 controls so all tubes were subcultured again into the same type of media. After a weeks incubation growth was determined by the decrease in media pH as described in Example 1.

Figure 2A:
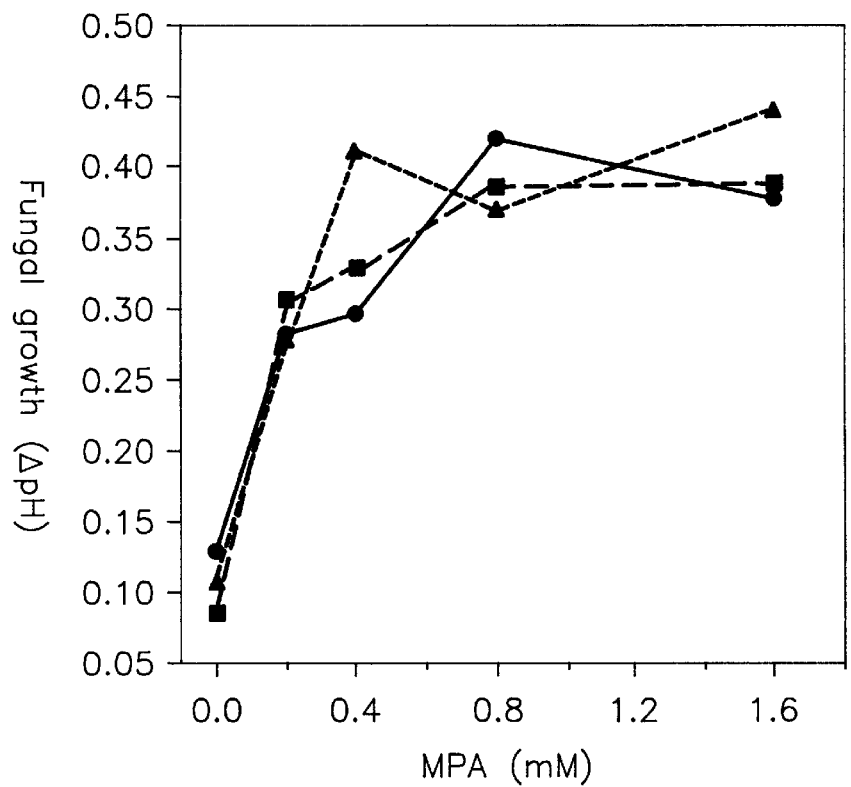
FIG. 2(a) illustrates the in vitro growth response of Neocallimastix isolates LM1 and TGB1.
Figure 2B:
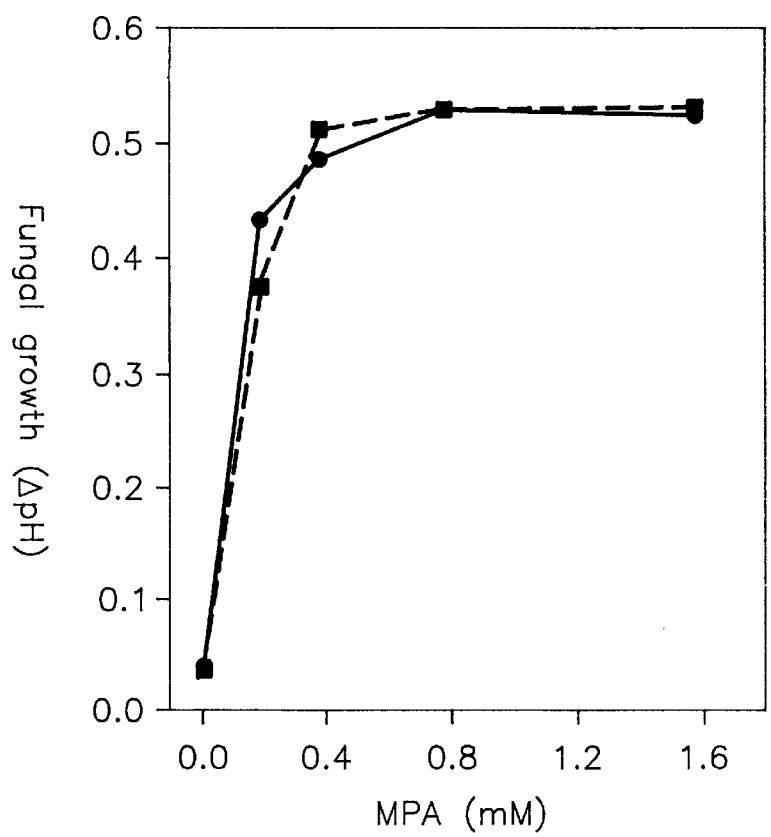
FIG. 2(b) illustrates the in vitro growth of Piromyces isolates SM1, CS15 and TZB2 using MPA as the sulphur source.

The result from the final series of media with 0.5% CHO is shown in FIGS. 2a and 2b. FIG. 2a shows the growth responses of the Neocallimastix isolates LM1 from sheep (●) and TGB1 from gemsbok (■). FIG. 2b shows the Piromyces isolates SM1 from sheep (●) CS15 from cattle (■) and TZB2 from zebra (▼). Although there was better growth of the Neocallimastix sp there was no clear difference between the sheep and non-sheep isolates in these results.

Example 4

The Effect of Different Doses of MPA on Fungal Numbers in the Rumen.

Sheep were fed alkali treated straw supplemented with minerals and urea but having a low sulphur content (0.052% sulphur) and infused with increasing levels of MPA directly into the rumen. After seven days on the same concentration of MPA the numbers of fungal zoospores in the rumen were determined by culture.

Six cross-bred sheep [wethers] having rumen cannula were moved metabolism cages equipped with automatic feeders. They were given eight equal buckets of feed a day (three hourly) and offered water ad-lib. The sheep were offered 1.1 kg of a low sulphur feed (see below).

After a period of three weeks on the diet rumen digesta was collected and rumen fluid (150 ml)was taken for zoospore counts. (An extra 100 ml of rumen digest was taken from each animal combined and mixed and 100 ml returned to each rumen to minimise differences between animals.) Zoospores were assessed by standard methods for handling anaerobic fungi. Serial dilutions of rumen fluid were prepared using an anaerobic diluent. Agar roll tubes were inoculated using a syringe with 0.2 ml of either a dilution of rumen fluid or undiluted rumen fluid. The media used was one mimicking the rumen environment but without added rumen fluid and with antibiotics (penicillin and streptomycin) added to stop overgrowth by rumen bacteria. After incubation the number of thallus forming units were counted and the number of zoospores in the rumen fluid calculated.

After sampling the infusion was begun by giving one days dose of MPA into the rumen and then starting the infusion ie infusion was at the rate of 48.5 ml/day using Palmer syringe pumps. The sheep were initially infused at the rate of 0.4 mMoles sulphur per day per 4 liters (ie 0.1 mM in rumen) This was equivalent to 12.67 mg Sulphur/day.

The same protocols were used with successively higher doses. The following doses were tested (given as rumen concentration and mg/d of sulphur): 0 (first sample); 0.1 mM [12.67]; 0.25 mM [31.7]; 0.35 mM [44.3]; 0.5 mM [63.3]; 0.75 mM [95]; 1.0 mM [126.7]; 1.5 mM [190]; 5.0 mM [633.3]. Each infusion was for one weeks before sampling rumen fluid and infusing the higher dose. A control period of one week with no infusion Was done after infusion with 95 mg Sulphur/d MPA and 4 of six sheep had no cultivable fungi with two having 1.7 thallus forming units/ml.

Wheat straw was milled and approximately 40 kg quantities were transferred from the Gell feed mill to a mixer where 4 l of 40% NaOH was added while mixing. The feed was bagged (approximately two bags per 40 kg) and left for several days before a minerals mix was added. Two bags were placed in the mixer and the compounds in Table 3 were added.

TABLE 3

| Compound | g/Kg |
| --- | --- |
| Urea | 22.0 |
| KCl* | 20.0 |
| $CaCO_3$ | 9.0 |
| $NH_4H_2PO_4$ | 8.0 |
| $MgCO_3$ | 2.0 |
| Trace Mineral Solution | |
| | mg/Kg |
| $ZnSO_4.H_2O$ | 108 |
| $FeCl_3$ | 87 |
| $MnSO_4.H_2O$ | 40 |
| $CuSO_4.5H_2O$ | 20 |
| $Na_2MoO_4$ | 3.8 |
| KI | 0.067 |

Trace elements were made up in 140 ml in water and were added to the urea which was previously dissolved in 25 Liters of water. This solution was then added to two bags of alkali treated feed while mixing. The remaining dry chemicals were mixed and the appropriate amount added (1.638 kg) onto the mixing feed. The feed was re-bagged into the original bags and left open for several weeks before the bags were tied shut.

Figure 3:
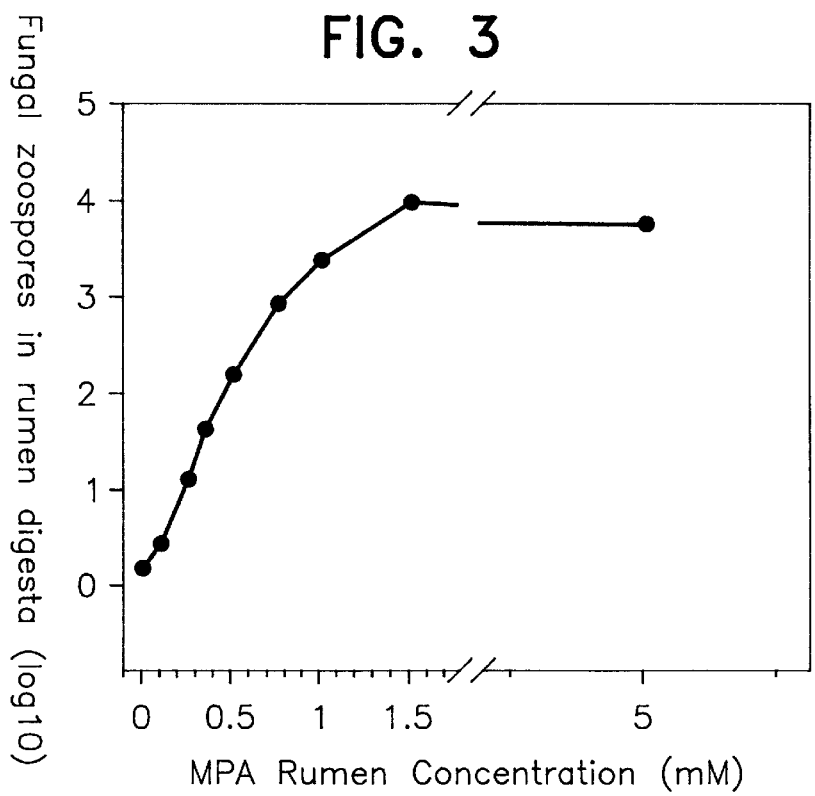
FIG. 3 illustrates the in vivo response of rumen fungi to varying concentrations of MPA.

The overall response can be seen in FIG. 3. There is a clear dose response between the concentration of MPA in the rumen and the numbers of zoospores found in rumen fluid. Four of the six animals had levels of fungi ($\approx$1000/ml) commonly seen in normal sheep at a dose of 0.75 mM (95 mg S/day). In subsequent experiments with diets having higher S content fungal numbers did not change as quickly. The optimum level of MPA of 1.5 mM (190 mg S)/day is likely to be affected by the very low S content of this diet.

Example 5

The Effect of MPA on Digestion and Rumen Microbiology

Feed was prepared as previously described (see example 4). Initially 22 sheep were fed 1 kg of alkali straw/day in the animal house for 4 days to select out sheep not eating the diet. 19 sheep were weighted and transferred to metabolism cages and feed the alkali straw diet ad-lib. Sheep were fed and on the following day the feed refusal weighted and if less then 100 g remained a further 100 g was fed; if 100–200g of feed remained the sheep was given the same amount of feed; if over 200 g of feed was left the sheep was given 100 g less feed.

Over the following week another 6 sheep were moved out of the experiment (usually due to very low or erratic intakes). Infusion of MPA was done as previously described (see example 4) with a constant dose rate of 6 mMoles/sheep/day. This dose [192mg Sulphur/day/sheep] was expected to give a intra-ruminal concentration of 1.5 mM MPA and was given to seven of fourteen sheep for 21 days. After 14 days infusion the collection period of 7 days commenced.

Feed refusals were weighted, recorded, and a sample of up to 200 g/day pooled for subsequent analyses. Spilt feed was collected daily, weighted, recorded, and discarded. Faeces were collected with separators that excluded urine. The faeces were weighed and sub-sampled and pooled for subsequent analyses. Pooled faeces and feed were stored at −20° C. and then dried in a hot air oven (faeces were initially dried at 70° C.) at 100° C. cooled and weighted to determine dry weight (DM).

At the end of the collection period samples of rumen digesta were taken for microbiology and other analyses. Rumen fluid was collected and fungal zoospores and total bacteria assessed as described in example 4 (the total bacteria were assessed on the same medium but without antibiotics). Cellulolytic bacteria were assessed by a most probable number count. Rumen fluid was serially diluted and subsamples of each dilution inoculated into 5 culture tubes containing an anaerobic medium containing rumen fluid and strips of filter paper. After incubation the presence of cellulolytic bacteria was detected by degradation of the paper and the numbers of positive tubes compared to tables to give a number of these bacteria in the original sample.

Following the last sampling the infusion was stopped in the first group of sheep and on the following day the infusion treatment was begun in the other group of seven sheep. The second period (the crossover) was conducted in the same way as the first period with the same samples being taken at the same times.

With the exception of one animal (which went off feed in the week preceding the non-infused collection period and rebounded during collection) there was a strong, positive, response in digestive performance (see Table 4) and to the numbers of rumen fungi to infusion by MPA. (see Table 5).

TABLE 4

Effect of MPA on Feed intake and digestibility
(MPA infused at 192 mg Sulphur/sheep/day)

| Sheep Tag | Intake DM (g/d) | | | Digestibility (% DM) | | | Digested DM (g/d) | | |
|---|---|---|---|---|---|---|---|---|---|
| | MPA | Control | % (+)[1] | MPA | Control | % (+)[1] | MPA | Control | % (+)[1] |
| 3009 | 1485 | 1356 | 9.6 | 48.119 | 48.117 | 0.002 | 714.69 | 652.25 | 9.57 |
| 2521 | 635 | 531 | 19.6 | 54.648 | 47.189 | 7.459 | 347.27 | 250.79 | 38.47 |
| 2509 | 805 | 581 | 38.6 | 51.522 | 43.723 | 7.799 | 414.97 | 254.10 | 63.31 |
| 2511 | 703 | 565 | 24.5 | 50.799 | 45.780 | 5.019 | 357.26 | 258.65 | 38.13 |
| 3017 | 1163 | 903 | 28.8 | 51.891 | 44.097 | 7.795 | 603.65 | 398.16 | 51.61 |
| 2520 | 1221 | 977 | 24.9 | 45.708 | 43.098 | 2.610 | 558.00 | 421.10 | 32.51 |
| 3012 | 983 | 736 | 33.5 | 52.812 | 51.359 | 1.453 | 518.94 | 378.00 | 37.28 |
| 2976 | 1389 | 1080 | 28.6 | 58.076 | 52.964 | 5.112 | 806.76 | 572.01 | 41.04 |
| 2492 | 1126 | 955 | 17.9 | 53.589 | 46.127 | 7.462 | 603.24 | 440.51 | 36.94 |
| 2516 | 1347 | 1142 | 18.0 | 46.808 | 44.264 | 2.544 | 630.64 | 505.49 | 24.76 |
| 3018 | 1288 | 1108 | 16.2 | 51.433 | 50.989 | 0.444 | 662.31 | 564.96 | 17.23 |
| 2997 | 1250 | 902 | 38.6 | 53.840 | 50.985 | 2.855 | 673.01 | 459.88 | 46.34 |
| 3010 | 1265 | 992 | 27.5 | 51.933 | 47.156 | 4.777 | 657.21 | 467.79 | 40.49 |
| Aver. n = 13 | 1128 | 910 | 25.1 | 51.6 | 47.37 | 4.26 | 581 | 433 | 36.75 |
| ± SD | 257 | 238 | 8.4 | 3.2 | 3.2 | 2.71 | 133 | 122 | 13.41 |

[1]% increase of intake in individual sheep after infusion of MPA

TABLE 5

Effect of MPA on Feed intake and microbiota
(MPA infused at 192 mg Sulphur/sheep/day)

| Sheep Tag | Intake DM (g/d) | | | Fungal Zoospores (per ml rumen fluid) | | | Total Bacteria ($\times 10^8$) | | | Cellutolytic Bacteria ($\times 10^8$) | | |
|---|---|---|---|---|---|---|---|---|---|---|---|---|
| | MPA | Control | % (+)[1] | MPA | Control | log (+)[2] | MPA | Control | log (+) | MPA | Control | log (+) |
| 3009 | 1485 | 1356 | 9.6 | 5383 | 533 | 1.0 | 6.33 | 13.83 | −0.34 | 18.37 | 4.42 | 0.62 |
| 2521 | 635 | 531 | 19.6 | 4900 | 401 | 1.1 | 10.50 | 8.37 | 0.10 | 3.22 | 1.086 | 0.47 |
| 2509 | 805 | 581 | 38.6 | 2567 | 5 | 2.7 | 10.50 | 5.70 | 0.27 | 6.96 | 1.837 | 0.58 |
| 2511 | 703 | 565 | 24.5 | 7083 | 25 | 2.5 | 8.07 | 3.93 | 0.31 | 0.556 | 1.837 | −0.52 |
| 3017 | 1163 | 903 | 28.8 | 3050 | 32 | 2.0 | 6.83 | 15.00 | −0.34 | 4.42 | 1.837 | 0.38 |
| 2520 | 1221 | 977 | 24.9 | 7283 | 38 | 2.3 | 7.50 | 11.00 | −0.17 | 1.84 | 3.219 | −0.24 |
| 3012 | 983 | 736 | 33.5 | 1783 | 766 | 0.4 | 10.00 | 9.5 | 0.02 | 2.173 | 1.84 | 0.07 |
| 2976 | 1389 | 1080 | 28.6 | 7250 | 2200 | 0.5 | 7.17 | 6.33 | 0.05 | 3.447 | 1.09 | 0.50 |
| 2492 | 1126 | 955 | 17.9 | 6167 | 1350 | 0.7 | 5.87 | 3.3 | 0.25 | 1.086 | 1.89 | −0.24 |
| 2515 | 1347 | 1142 | 18.0 | 4417 | 683 | 0.8 | 12.00 | 6.2 | 0.29 | 0.912 | 0.696 | 0.12 |
| 3018 | 1288 | 1108 | 16.2 | 9017 | 6016 | 0.2 | 14.50 | 8.17 | 0.25 | 3.219 | 0.0556 | 1.76 |
| 2997 | 1250 | 902 | 38.6 | 6467 | 1717 | 0.6 | 10.83 | 5.07 | 0.33 | 3.219 | 0.556 | 0.76 |
| 3010 | 1265 | 992 | 27.5 | 11167 | 1183 | 1.0 | 10.67 | 5.17 | 0.31 | 3.219 | 0.322 | 1.00 |
| Aver. (n = 13) | 1128 | 910 | 25.1 | 5887 | 1150 | 1.20 | 9.29 | 7.81 | 0.10 | 4.05 | 1.59 | 0.40 |
| ± SD | 257 | 238 | 8.4 | 2521 | 1556 | 0.82 | 2.45 | 3.51 | 0.24 | 4.28 | 1.11 | 0.55 |

[1] % increase of intake in individual sheep after infusion of MPA
[2] log10 increase in individual sheep after infusion of MPA General Materials and Methods used in Examples
Media for growth of anaerobic fungi (and rumen bacteria when antibiotics not included).

Mix the solutions and ingredients of basal medium in the order given in Table 6 and dissolve the solids. Add the four carbon sources listed in Table 7 to make medium 10X. Boil the mixture for 5 min in a suitable glass vessel with a narrow neck (e.g. a 150-ml heat-resistant conical flask for a 100 ml quantity of medium), add 1 ml fresh reducing solution (see footnote to Table 6 for composition) for each 100 ml medium. Bubble a gentle stream of $CO_2$ through the medium with the vessel in an ice bath until the liquid is cold, i.e. 0–4° C. About 15 min is adequate for 100 ml but a longer time is required to cool larger volumes of media. The colour of the medium will change from pink (oxidized resazurin) to colourless (reduced). At this stage, the pH of the medium is measured and should be in the range 6.4–6.8 before dispensing the medium. A medium with a pH of greater than 6.8 will probably respond to continued bubbling with $CO_2$. Medium with a pH value that is much below 6.4 is likely to be faulty and should be remade. Reduced medium is dispensed into Hungate tubes or other appropriate vessels [Hungate tubes are screw-capped test tubes (16 mm diameter) and are supplied by Bellco Glass Incorporated (Vineland, N.J., U.S.A.; catalogue number 2047), they are used in conjunction with butyl rubber septa and screw caps obtained from the same source]. Sterilize the medium by autoclave at 120° C. for 15 min.

To make a broth medium for maintenance of cultures, dispense 5 ml under $CO_2$ into each Hungate tube which already contains 2.5 mg agar (added as a small aliquot of a molten agar solution). Cap and seal as before and autoclave. Disperse the agar through the medium while it is still warm by gently inverting the tubes several times.

Antibiotic solution

Benzyl penicillin (12 mg/ml) and streptomycin sulphate (2 mg/ml) are dissolved in distilled water which has been previously boiled for 5 min and bubbled with a gentle stream of $N_2$ until cooled. The antibiotic (pen-strep) solution is filter sterilized (a membrane with pores of 0.2 $\mu$m) whilst being gassed with $N_2$. Store the solution in a closely capped bottle, under $N_2$, at 4° C. for up to 5 d. A mixture of lincomycin HCl (1 mg/ml) and chloramphenicol succinate (0.42 mg/ml) is made and sterilized in the same manner.

Anaerobic Dilution Solution (ADS)

Combine all components listed in Table 8 and boil the solution for 5 min. Add 1 ml freshly prepared reducing solution per 100 ml (see footnote to Table 6). Bubble the medium with $CO_2$ on ice until the liquid is cold. Dispense exactly 9.0 ml under $CO_2$ into Hungate tubes (see section 5.2), seal with butyl rubber septa and screw caps. Autoclave at 120° C. for 15 min. Prepared ADS sometimes has a white precipitate at the bottom of the tubes when hot, The precipitate redissolves upon gentle mixing of the cooled ADS. The final pH of ADS is about 6.2.

Agar roll tubes

Roll tubes are prepared by dispensing 2.8 ml medium 10X into Hungate tubes which already contain 60 mg agar powder (Oxoid Limited, Basingstoke, Hampshire, England) and are being flushed with a gentle stream of $CO_2$. Alternatively, agar roll tubes can be prepared in rimless, thick-walled test tubes fitted with black butyl rubber stoppers by adjusting the volume of medium to match the capacity of the tubes. The roll tubes are sterilized in an autoclave for 15 min at 120° C. Hold these tubes of molten agar medium in a water bath at 52–55° C. and add 0.3 ml fresh penstrep antibiotic solution to each by means of a sterile disposable 2-ml syringe (and 25 gauge needle) about 30 min before the tubes will be used. Do not hold these tubes around 55° C. for longer than overnight as the agar will become partly hydrolysed.

Zoospore counts by agar roll tubes

The number of zoospores in samples of strained ruminal fluid can be used to follow zoosporogenesis in the rumen and it provides a relative estimate of the size of the anaerobic fungal population.

(1) Strain a sample of ruminal digesta through an open weave cloth, and collect the filtered fluid in a $CO_2$-filled flask.

(2) Serially dilute the fluid ten-fold in anaerobic dilution solution (ADS) to a final dilution of $10^{-3}$. To do this, transfer 1 ml volumes using 1 ml disposable sterile syringes fitted with sterile 23 gauge (0.65 mm) needles to tubes containing 9 ml ADS, starting with fluid to form the $10^{-1}$ dilution. Use a clean syringe at each dilution step.

(3) Using a 1 ml syringe (and 23 ga. needle, as before) inoculate three roll tubes each with 0.2 ml of $10^{-3}$ dilution. Immediately roll these tubes horizontally on ice until the agar sets. With the same syringe, inoculate three more roll tubes with 0.2 ml of $10^{-2}$ dilution and roll them. Repeat with $10^{-1}$ dilution and finally with undiluted fluid, if appropriate.

(4) Incubate the roll tubes vertically at 39° C. for 5 d. Count the total number of fungal colonies growing in each tube and use the inoculum volume (0.2 ml) and the dilution value (1, 0.1, 00.1 or 0.001) to calculate the number of fungal zoospores per ml of original fluid.

TABLE 6

Composition of liquid basal medium for anaerobic fungi

| Solution or ingredient | Component(s) or source | Concentration or proportion in solution | Quantity per 100 ml medium |
|---|---|---|---|
| Mineral solution I | $K_2HPO_4$ | 3.0 g/l | 15 ml |
| Mineral solution II | $KH_2PO_4$ | 1.0 g | |
| | NaCl | 6.0 g | |
| | $(NH_4)_2SO_4$ | 6.0 g | |
| | $CaCl_2.2H_2O$ | 0.8 g | |
| | $MgCl_2.6H_2O$ | 1.0 g/l | 15 ml |
| Redox indicator solution | resazurin | 1.0 g/l | 0.1 ml |
| Haemin solution | haemin | 0.5 g | |
| | NaOH | 2.0 g/l | 0.2 ml |
| Volatile fatty acids | acetic | 17 ml | |
| | propionic | 6 ml | |
| | n-butyric | 4 ml | |
| | i-butyric | 1 ml | |
| | n-valeric | 1 ml | |
| | i-valeric | 1 ml | |
| | DL-2-methyl-butyric | 1 ml | 0.31 ml |
| | Total | 31 ml | |
| Carbonate solution | $Na_2CO_3$ | 80 g/l | 7 ml |
| Yeast extract | Oxoid[a] | — | 0.05 g |
| Peptone | "Tryptone", Oxoid[a] | — | 0.2 g |

[a]Oxoid, Basingstoke, UK

Reducing solution: Dissolve 0.625 g cysteine-HCl in 24 ml distilled water, adjust pH to 11 with 10 M NaOH. Add 0.625 g $Na_2S.9H_2O$, dissolve, and boil immediately before use. Make fresh reducing solutions for each batch of basal medium.

TABLE 7

Composition of medium 10X

| Components | Amount |
|---|---|
| Basal medium 10 | 100 ml |
| Glucose | 33 mg |
| Cellobiose | 33 mg |
| Starch (from wheat) | 67 mg |
| Xylan | 67 mg |

TABLE 8

Composition of Anaerobic Dilution Solution (ADS)

| Component | Volume (ml) |
|---|---|
| Mineral solution I[a] | 15.0 |
| Mineral solution II[a] | 15.0 |
| Resazurin (0.1% aqueous) | 0.1 |
| $Na_2CO_3$ (8% aqueous) | 3.8 |
| Distilled water | 66.1 |

[a]The composition of Mineral solutions I and II are given in Table 6.

The present invention includes within its scope adaptations and modifications apparent to one skilled in the art.

What is claimed is:

1. A method for promoting the growth of at least one anaerobic fungus in the rumen of a ruminant animal, the method comprising the step of administering to the rumen an effective amount of 3-mercaptopropanoic acid (MPA) or a functional equivalent thereof.

2. The method according to claim 1, wherein the funcitional equivalent is selected from the group consisting of: a salt of MPA with monovalent and divalent cations; an ester of MPA incorporating an alkyl group; and the dimer form of MPA.

3. The method according to claim 2, wherein the salt of MPA is a sodium, potassium, calcium, copper, zinc or magnesium salt.

4. The method according to claim 2, wherein the ester of MPA incorporates an alkyl group selected from the group consisting of methyl, ethyl and butyl groups.

5. The method according to claim 1, wherein the MPA or functional equivalent thereof is administered intraruminally.

6. The method according to claim 5, wherein the MPA or functional equivalent thereof is administered using a controlled release device.

7. The method according to claim 1, where the MPA or functional equivalent thereof is administered orally.

8. The method according to claim 1, wherein the effective dose of MPA or functional equivalent thereof is such that the concentration of MPA or functional equivalent thereof in the rumen is 0.2 mM to 8 mM.

9. The method according to claim 1, wherein the effective dose of MPA or functional equivalent thereof is such that the concentration of MPA or functional equivalent thereof in the rumen is 0.2 to 4 mM.

10. The method according to claim 1, wherein the effective dose of MPA or functional equivalent thereof is such that the concentration of MPA or functional equivalent thereof in the rumen is 0.75 to 1.5 mM.

11. The method according to claim 1, wherein the effective dose of MPA or functional equivalent thereof is 25–200 mg Sulphur/day.

12. The method according to claim 1, wherein the effective dose of MPA or functional equivalent thereof is 95–109 mg Sulphur/day.

13. The method according to claim 1, wherein the effective dose of MPA or functional equivalent thereof is 190 mg sulphur/day.

14. A veterinary preparatior comprising MPA or a functional equivalent thereof and a suitable carrier.

15. The veterinary preparation according to claim 14, wherein the functional equivalent is selected from the group consisting of: a salt of MPA with monovalent and divalent cations; an ester of MPA incorporating an alkyl group; and the dimer form of MPA.

16. The veterinary preparation according to claim 15, wherein the salt of MPA is a sodium, potassium, calcium, copper, zinc or magnesium salt.

17. The veterinary preparation according to claim 15, wherein the ester of MPA incorporates an alkyl group selected from the group consisting of methyl, ethyl and butyl groups.

* * * * *